US00PP15558P2

(12) United States Plant Patent
Brown

(10) Patent No.: US PP15,558 P2
(45) Date of Patent: Feb. 15, 2005

(54) ***IMPATIENS* PLANT NAMED 'COBIMPTO'**

(50) Latin Name: *Impatiens walleriana*
Varietal Denomination: Cobimpto

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 0 days.

(21) Appl. No.: 10/822,985

(22) Filed: Apr. 13, 2004

(51) Int. Cl.[7] ..... A01H 5/00

(52) U.S. Cl. ..... Plt./317

(58) Field of Search ..... Plt./317

(56) References Cited

PUBLICATIONS

UPOV ROM GTITM Computer Database, GTI Jouve Retrieval Software 2004/02 citation(s) for Cobimpto.*
Email from Tanvir.Hossain@affa.gov.au dated Tuesday, Jul. 27, 2004.*
Plant Varieties Journal vol. 16 No. 1 Quarter One 2003 May 16, 2003, pp. 1, 12, 22–23.*
Results of Plant Varieites Journal website search.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of Double *Impatiens* plant named 'Cobimpto', characterized by its compact, mounded and outwardly spreading plant habit; freely basal branching habit; dark green leaves; large red purple-colored flowers; fully double flower form; freely flowering habit; and flowers positioned above and beyond the foliage.

1 Drawing Sheet

Botanical classification: *Impatiens walleriana* cultivar Cobimpto.

BACKGROUND OF THE INVENTION

The present Invention relates to a new and distinct cultivar of *Impatiens* plant, botanically known as *Impatiens walleriana*, commercially known as Double *Impatiens*, and hereinafter referred to by the name 'Cobimpto'.

The new *Impatiens* is a naturally-occurring whole plant mutation of the Double *Impatiens* cultivar Codimpca, not patented. The new *Impatiens* was discovered and selected by the Inventor as a flowering plant from within a population of plants of 'Codimpca' in a controlled environment in Cobbitty, New South Wales, Australia in 1999.

Asexual reproduction of the new cultivar by terminal cuttings taken at Macquarie Fields, New South Wales, Australia since December 1999, has shown that the unique features of this new *Impatiens* are stable and reproduced true to type in successive generations of asexual reproduction.

SUMMARY OF THE INVENTION

The following traits have been repeatedly observed and are determined to be the unique characteristics of 'Cobimpto'. These characteristics in combination distinguish 'Cobimpto' as a new and distinct cultivar:

1. Compact, mounded and outwardly spreading plant habit.
2. Freely basal branching habit.
3. Dark green leaves; densely foliated.
4. Large red purple-colored flowers.
5. Fully double flower form.
6. Freely flowering habit.
7. Flowers positioned above and beyond the foliage.

Plants of the new *Impatiens* differ from plants of the parent, the cultivar Codimpca primarily in flower coloration as flowers of plants of the female parent are pink in color.

Plants of the new *Impatiens* can be compared to plants of the *Impatiens* cultivar Fiesta Violet, not patented. Plants of the new *Impatiens* differ primarily from plants of the cultivar Fiesta Violet in time to flower as plants of the new *Impatiens* flower about one week earlier than plants of the cultivar Fiesta Violet.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*.

The photograph at the bottom of sheet comprises a side perspective view of a typical flowering plant of 'Cobimpto' grown in a 15-cm container for about 12 weeks.

The photograph at the top of the sheet comprises a close-up view of typical developing flowers and leaves of 'Cobimpto'.

DETAILED BOTANICAL DESCRIPTION

The cultivar Cobimpto has not been observed under all possible environmental conditions. The phenotype may vary somewhat with variations in environment such as temperature and light intensity without, however, any variance in genotype. Plants used in the aforementioned photographs and for the following description were grown in Lompoc, Calif., under commercial practice during the winter in a polycarbonate-covered greenhouse with day temperatures about 18 to 24° C., night temperatures about 16 to 18° C. and light levels about 4,000 to 8,000 foot-candles. Unrooted cuttings were directly planted in 15-cm containers and grown for about 17 weeks. In the following description, color references are made to The Royal Horticultural Society Colour Chart, 1995 Edition, except where general terms of ordinary dictionary significance are used.

Botanical classification: *Impatiens walleriana* cultivar Cobimpto.

Parentage: Naturally-occurring whole plant mutation of the *Impatiens walleriana* cultivar Codimpca, not patented.

Propagation:

*Type cutting*.—Terminal cuttings.

*Time to initiate roots*.—About 10 to 14 days at 21° C.

*Time to produce a rooted cutting or liner*.—About 21 to 28 days at 21° C.

*Root description*.—Fine, fibrous; white in color.

*Rooting habit*.—Freely branching; dense.

Plant description:

*General appearance*.—Compact, mounded and outwardly spreading.

*Growth and branching habit*.—Moderately vigorous and freely-basal branching with about 15 lateral branches developing at the base; dense and bushy growth. Pinching, that is, removal of the terminal apices, will enhance branching.

*Crop time*.—About eight weeks are required to produce a finished flowering plant from planting an unrooted cutting in a 15-cm pot.

*Plant height*.—About 12 cm.

*Plant diameter or spread*.—About 36 cm.

*Lateral branches*.—Length: About 14 cm. Diameter: About 7 mm. Internode length: About 2.25 cm. Texture: Smooth. Color: 195A overlain with 187B.

*Foliage description*.—Arrangement: Simple, alternate. Length: About 3.8 cm. Width: About 2.8 cm. Shape: Elliptic. Apex: Acuminate. Base: Attenuate. Margin: Scalloped; sparsely ciliate. Texture, upper and lower surfaces: Glabrous, smooth. Venation pattern: Pinnate, arcuate. Color: Developing and fully expanded foliage, upper surface: 147A. Developing and fully expanded foliage, lower surface: 147B. Venation, upper surface: 146B. Venation, lower surface: 146A. Petiole: Length: About 1.3 cm. Diameter: About 2 mm. Color: 195A.

Flower description:

*Flower type and habit*.—Numerous and consistently large fully double flowers. Freely and continuously flowering. Flower buds open similar to a rose in fullness; flowers rounded. Flowers arise from leaf axils. Typically about 30 flowers and flower buds per lateral branch. Flowers positioned above and beyond the foliage and typically face upward and outward. Flowers last about five to seven days under greenhouse conditions. Flowers not persistent. Flowers not fragrant.

*Flowering season*.—Year-round under greenhouse conditions. In the garden, flowering in continuous from spring until fall.

*Flower size*.—Diameter: About 3.8 cm. Depth: About 2 cm.

*Flower buds*.—Length, at stage of showing color: About 1.5 cm. Diameter, at stage of showing color: About 1.2 cm. Shape: Rounded to ovoid. Color: 70B.

*Petals*.—Quantity/arrangement: About 36 per flower; imbricate. Length, outer petals: About 2 cm. Width, outer petals: About 2.2 cm. Shape: Obovate to cordate. Apex: Rounded to occasionally emarginate. Base: Acute. Margin: Entire. Texture, upper and lower surfaces: Velvety, smooth. Color: When opening, upper surface: 66A. When opening, lower surface: 72C. Fully opened, upper surface: 74A; color becoming closer to 78A with development. Fully opened, lower surface: 74A.

*Spurs*.—Length: About 3 cm. Diameter, at flower: About 2.5 mm. Diameter, at apex: Less than 1 mm. Color: 146D.

*Sepals*.—Quantity/arrangement: Five in a single whorl. Calyx length: About 1.1 cm. Calyx diameter: About 1 cm. Shape: Elliptic. Apex: Broadly acute. Margin: Entire. Texture, upper and lower surfaces: Smooth. Color: Upper surface: 145D. Lower surface: 145C.

*Peduncles*.—Length: About 2.2 cm. Diameter: About 2 mm. Angle: About 45 to 55° to the lateral branch. Strength: Strong. Color: 195A.

*Reproductive organs*.—None observed.

*Seed/fruit*.—Seed and fruit development has not been observed.

Disease/pest resistance: Plants of the new *Impatiens* have not been observed to be resistant to pathogens and pests common to *Impatiens*.

It is claimed:

1. A new and distinct cultivar of Double *Impatiens* plant named 'Cobimpto', as illustrated and described.

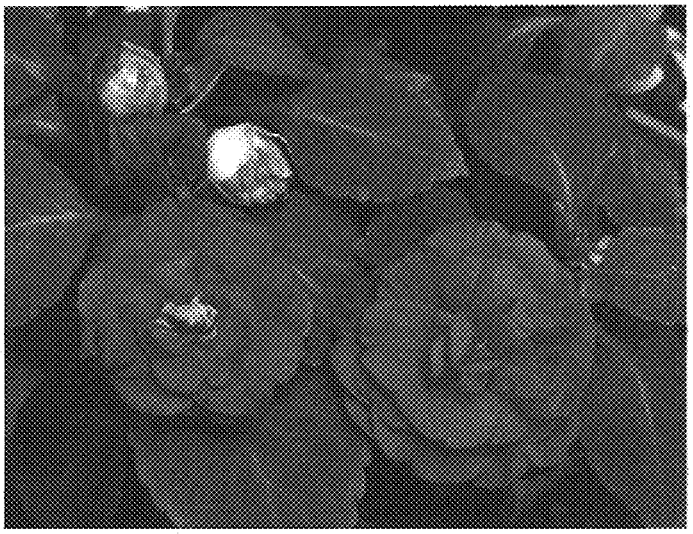
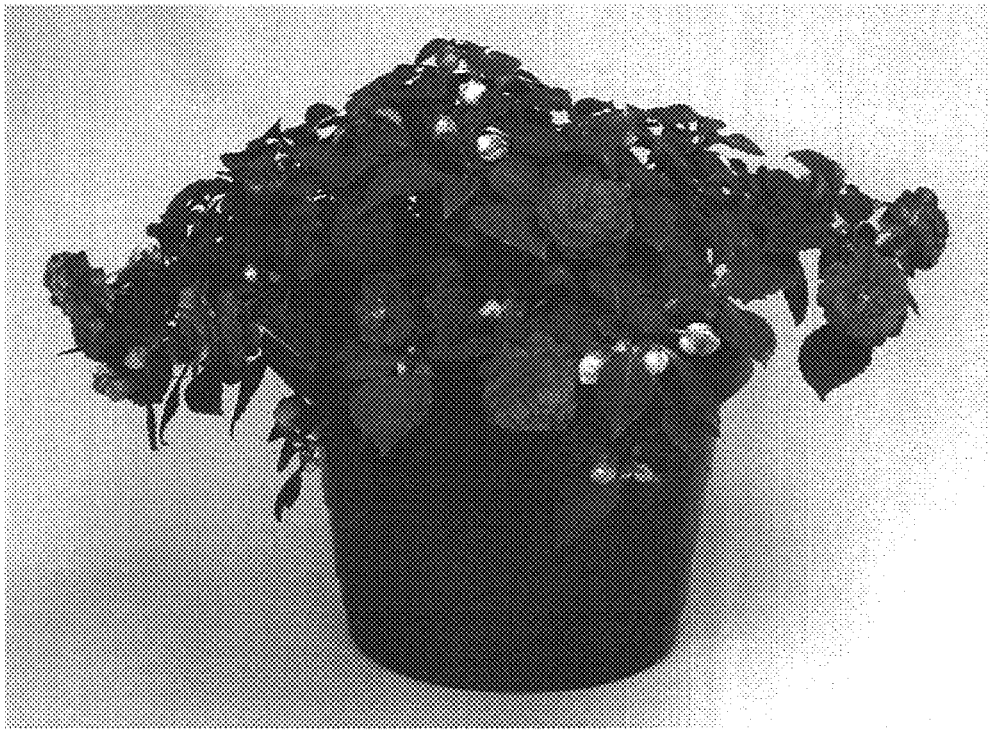

* * * * *